United States Patent [19]

Schramm

[11] Patent Number: 4,826,491

[45] Date of Patent: * May 2, 1989

[54] NEEDLE BEARING MEDICAL DEVICE WITH THREE-POSITION SHIELD

[76] Inventor: James J. Schramm, 1807 E. Grand Ave., Lindenhurst, Ill. 60046

[*] Notice: The portion of the term of this patent subsequent to Jun. 21, 2005 has been disclaimed.

[21] Appl. No.: 175,310

[22] Filed: Mar. 30, 1988

Related U.S. Application Data

[63] Continuation-in-part of Ser. No. 78,386, Jul. 27, 1987, Pat. No. 4,752,290.

[51] Int. Cl.⁴ ............................................. A61M 5/32
[52] U.S. Cl. .................................... 604/198; 604/263
[58] Field of Search ............... 604/187, 192, 197, 198, 604/263, 110

[56] References Cited

U.S. PATENT DOCUMENTS 4,752,290  6/1988  Schramm ........................... 604/198

Primary Examiner—John D. Yasko
Attorney, Agent, or Firm—Marshall, O'Toole, Gerstein, Murray & Bicknell

[57] ABSTRACT

Needle-containing medical appliances (e.g., hypodermic syringes, i.v. catheter placement units and phlebotomy apparatus) having tubular shields which are adapted to protect users from injury from contact with the needle are disclosed and claimed. A series of raked teeth on the tubular shield cooperate with raised surfaces on the body of the medical appliance to provide three distinct shield-retaining positions, one of which is adapted to lock the shield around the needle in a substantially non-releasable position.

11 Claims, 3 Drawing Sheets

NEEDLE BEARING MEDICAL DEVICE WITH THREE-POSITION SHIELD

RELATED APPLICATIONS

This is a continuation-in-part of application Ser. No. 78,386, filed July 27, 1987, U.S. Pat. No. 4,752,290.

BACKGROUND OF THE INVENTION

The present invention provides an improved needle-guard assembly for medical devices which are used, for example, in the administration of drugs or for the withdrawal of blood. More particularly, tee invention relates to needle-bearing medical appliances, such as hypodermic syringes, i.v. catheter placement units, phlebotomy (blood-collecting) apparatus and the like, furnished with retractable, tubular shields designed to protect the needle portion of such devices prior to use, and to be locked around the needle after use in order to prevent injury from accidental contact.

Needle-bearing devices which are utilized for the subcutaneous or intramuscular injection of medicaments, or for insertion into a blood vessel are generally manufactured in disposable form so as to reduce the risk of patient infection. One group which remains at risk in dealing with such devices are health care professionals and housekeeping personnel who must handle these skin-puncturing devices after they have been used. Contaminated needles present a substantial health hazard and can result in transmission of a number of potentially life-threatening diseases.

That this problem has been recognized in the art is evidenced by the number of patents which have issued directed to apparatus for shielding needles after use, for example, U.S. Pat. Nos. 3,890,971, 4,139,009, 4,507,117 and 4,592,744. Of particular interest to the background of the present invention are three United States patents which employ retractable, tubular shields adapted to surround the needle portion of a disposable hypodermic syringe after it has been used—U.S. Pat. Nos. 4,425,120, 4,573,976 and 4,631,057.

U.S. Pat. No. 4,425,120 (Sampson et al) describes a hypodermic syringe having a tubular shield which is designed to be locked in either a needle-shielding position or a retracted position. The shield is held in either of these two positions by means of upstanding pins on the syringe body which are adapted to cooperate with tracks formed in the shield. Locking is accomplished by rotating the shield so that the pin is held by an offset at the terminus of the track.

A later Sampson et al patent, U.S. Pat. No. 4,573,976, depicts a syringe having a tubular shield equipped with an upstanding catch which is designed to hold the shield in either a needle-covering or a needle-exposed position. The device shown in this patent is said to be an improvement over the apparatus shown in the patentees' earlier U.S. Pat. No. 4,425,120 patent in that locking and unlocking can be accomplished without rotational movement of the shield.

U.S. Pat. No. 4,631,057 illustrates a third injury-preventing adaptation which permits movement of a tubular guard on a syringe body between needle-covering and needle-exposing positions. The guard is held in either of these positions by means of a collar located adjacent the distal end of the syringe barrel. The collar has circumferential indentations which are adapted to cooperate with projections on the interior of the tubular guard. This design permits easy disengagement of the guard from the latched position when the guard is in the retracted (needle-exposed) position. However, when the guard is in the extended (needle-covering) position, the shield is held in a substantially permanent locked condition. Prior to being used to dispense a liquid medication, a separate shield is required to cover the needle.

SUMMARY OF THE INVENTION

The present invention provides a needle-bearing medical device having a tubular shield which is adapted to be held in three positions: a first, releasable, needle-covering position; a second, releasable, needle-exposing position; and, a third, non-releasable, needle-covering position. The apparatus is relatively simple in construction and conventional hypodermic syringes, phlebotomy apparatus, intravenous catheter placement units or other elongated medical devices having internal liquid passageways can be readily modified to incorporate such three-position shields.

The first, needle-covering position can be used to protect the needle prior to use with a patient, e.g., during shipment. In this condition, an intermediate ridge or annular retaining ring on the barrel of the medical device cooperates with raked teeth located at one end of the protective shield, on an interior surface thereof, to hold the shield in position over the needle. To use the apparatus, a medical provider would remove any optional safety cap covering the open end of the shield and slide the shield back, out of engagement with the intermediate ridge, and into engagement with a second ridge or annular retaining ring located on the distal end of the medical device away from (distal to) the needle.

The three-position shield of the present invention makes it possible to dispense with a separate, needle-covering sheath which is customarily used with these types of medical appliances. However, if a separate needle sheath is employed, it can be removed after movement of the shield to the needle-exposing position. The medical device can then be used in the normal manner.

After use with a patient, the needle portion of the medical device will be contaminated. In order to protect those who subsequently come in contact with the apparatus, the medical device of the present invention is adapted so that the protective shield can be locked firmly over the needle portion. This is accomplished by advancing the shield forward, in the direction of the needle, out of engagement with the distal retaining ridge and past the intermediate retaining ridge, into contact with a raked tooth or series of raked teeth which are provided on the proximal end of the medical device (adjacent the needle).

The teeth on the body of the medical device are adapted to cooperate with the series of teeth on the protective shield to lock the shield firmly over the needle. The angles of these two sets of teeth are such that movement of the shield in the direction of the needle is easily accomplished until full engagement has been made (evidenced by a ratcheting sound as the teeth engage). The angular orientation of the outwardly-extending teeth on the body of the medical device causes them to act like a series of bearing surfaces, permitting movement of the raked teeth on the shield over the tooth or teeth on the body when the shield is moved in the direction of the needle. However, movement in the opposite direction (away from the needle) is impeded by the inter-locking of the teeth on the two surfaces. When the two sets of teeth have engaged with one another, the shield can be withdrawn from its locked position over the needle only by the application of a strong force or by the use of a tool. In this condition, the shield is relatively non-releasable.

In a preferred embodiment, the tubular shield is provided with one or more cut-outs along the shield periphery. The cut-out allows the shield to be more easily mounted around the body of the medical device, simplifying construction. Another advantage of the cut-out is that it permits a greater range of motion for the teeth on the shield. As a result, the teeth do not have to be cut to close tolerances.

The protective shield is preferably manufactured from a resilient, transparent material. A clear acrylic or polyethylene plastic material which can be formed into the required shape by an injection molding process is especially suitable, although other materials and forming methods can be employed.

Although the apparatus of the present invention is particularly suitable for use with disposable syringes, i.v. catheter placement units, blood collection apparatus and the like, it can be adapted for use with re-usable, needle-containing medical devices which may have been contaminated through contact with blood or other fluids. The shield cut-outs facilitate removal of the tubular protective shield with a tool (either prior or subsequent to sterilization) so that the apparatus can be re-used, if appropriate.

The invention may best be understood by reference to the following description when considered with the accompanying illustrative drawings.

DETAILED DESCRIPTION OF THE DRAWINGS

Figure 1:
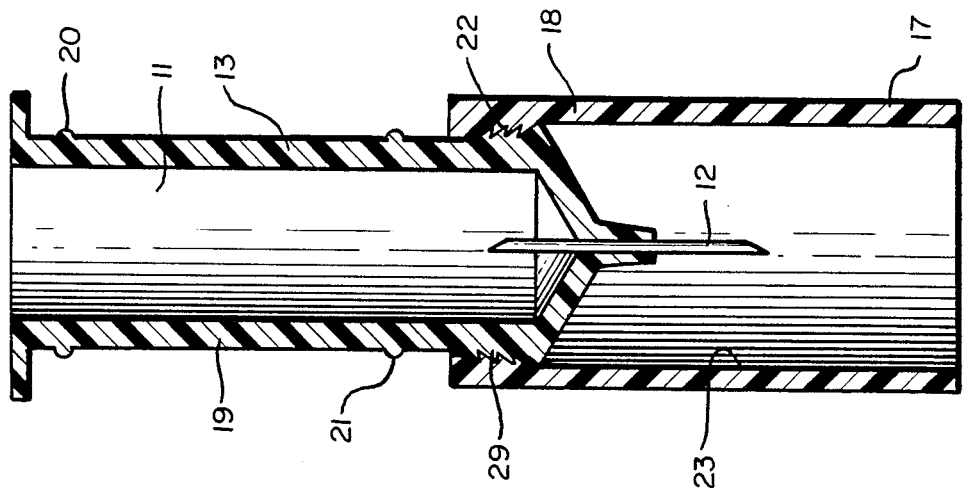
FIG. 1 is an elevational view, partly in section, of a phlebotomy tube having a tubular protective shield in a first, releasable, needle-covering position.

Referring to FIGS. 1-4, a disposable, phlebotomy tube of the type used for withdrawing blood samples is indicated generally by the numeral 10. Phlebotomy tube 10 is an elongated structure, manufactured from a thermoplastic material by conventional molding processes, having an internal chamber 11, defined by both a cylindrical wall 13 and a base section 14 which is located proximately to a hollow needle 12. Needle 12 has an exterior terminus or point 25 and an interior terminus 26 which is located inside chamber 11, opposite point 25. Needle 12 is fixedly held in position by an annular, needle-mounting sleeve portion 15 of chamber base section 14 so that needle 13 lies substantially along the major axis of the phlebotomy tube.

Phlebotomy tube 10 includes a tubular protective shield 16 having a first end portion 17 and a second end portion 18. Rows of angular, inwardly-depending raked teeth 22 extend circumferentially around an interior surface 23 of shield 16, adjacent the second end portion 18 thereof. Shield 16 is also formed of a thermoplastic material, and teeth 22 are formed therein during the molding process.

Outer surface 19 of cylindrical wall 13 is provided with thermoformed distal retaining ring 20 and intermediate retaining ring 21 for cooperating with raked teeth 22 to releasably hold protective shield 16 in needle-covering or needle-exposing positions, respectively.

FIG. 1 depicts phlebotomy tube 10 in a first, needle-covering position with protective shield 16 surrounding needle 12. Inwardly-depending raked teeth 22 are engaged by intermediate ring 21 to maintain shield 16 in the closed position. Ring 21 and teeth 22 can be disengaged by the application of either upward or downward pressure to shield 16.

In order to utilize tube 10, the operator must first remove protective cap 27 which covers the opening of shield end portion 17. Shield 16 may then be retracted, in the direction of distal retaining ring 20, into the needle-exposing position of FIG. 2. A flange 34 prevents removal of shield 16 when it is moved to the retracted position.

Figure 2:
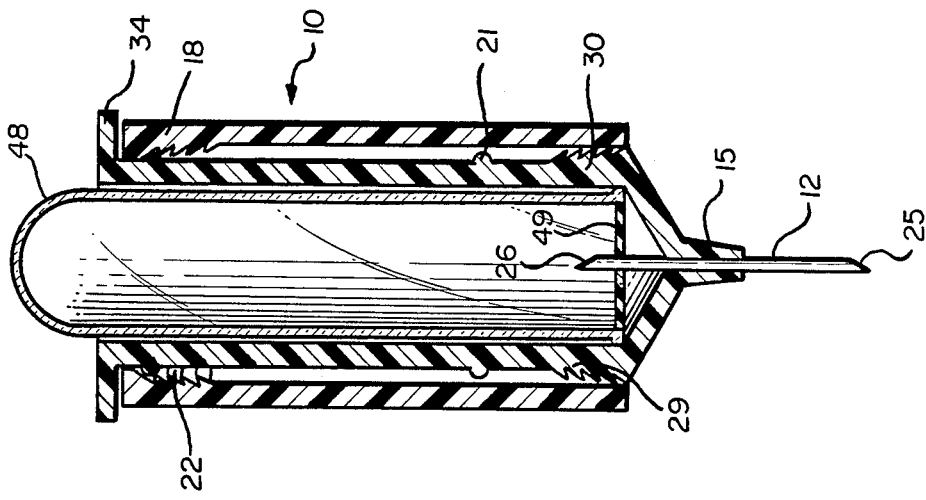
FIG. 2 is an elevational view, partly in section, showing the phlebotomy apparatus of FIG. 1 having the protective shield in a second, releasable, needle-exposing position with a blood collection tube mounted inside the phlebotomy apparatus.

FIG. 2 shows tube 10 in the second, needle-exposing position. Raked teeth 22 cooperate with distal retaining ring 20 to releasably hold shield 16 in place. After removal of an optional protective sheath (not shown) from needle 12, the phlebotomy tube is ready for use. When needle point 25 is inserted into a blood vessel, blood will flow through hollow needle 12 and into a partially evacuated blood collection tube 48 which is removably mounted inside phlebotomy tube internal chamber 11.

Collection tube 48 has a reasonable elastomeric shield 49 at the proximal end thereof which, in the position shown in FIG. 2, is pierced by needle interior terminus 26. Tube 48 provides both a passageway for the blood being sampled and as a container for holding the blood pending analysis.

After a sufficient quantity of blood has been collected in one or more tubes 48, needle point 25 is removed from the patient's blood vessel. Because needle point 25 may be contaminated with pathogens, tube 10 is adapted to prevent injury to personnel who subsequently come into physical contact with the apparatus.

Figure 3:
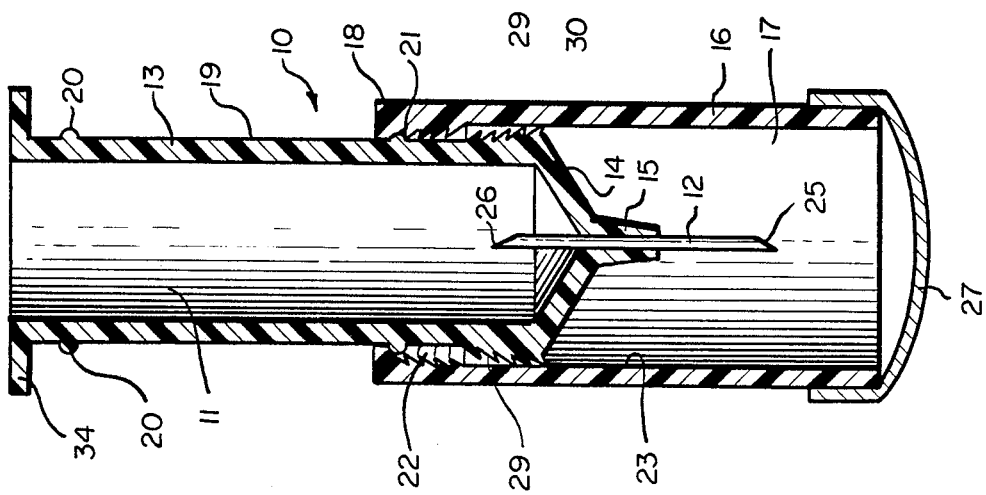
FIG. 3 is an elevational view, partly in section, showing the phlebotomy apparatus with the protective shield in a third, non-releasable, needle-covering position.

Protection is accomplished by moving shield 16 from the needle-exposing position of FIG. 2 to a third, needle-covering position of FIG. 3. In this latter position, shield 16 has been advanced downward, in the direction of needle 12, so that downwardly-depending raked teeth 22 on shield 16 are advanced past intermediate ring 21 (the FIG. 1 position), and into lockable engagement with a series of outwardly-extending raked teeth 29 located circumferentially around the distal end section 30 of cylindrical wall 13. Raked teeth 22 and 29 are disposed at acute, complimentary angles which allows movement of shield 16 from the position of FIG. 2 to that of FIG. 3, but resists movement of the shield in the opposite direction. The fact that tube 10 has been used can be ascertained both from the position of shield 12 with respect to wall 13 and by the fact that the shield cannot be moved to a needle-exposing position.

Figure 4:
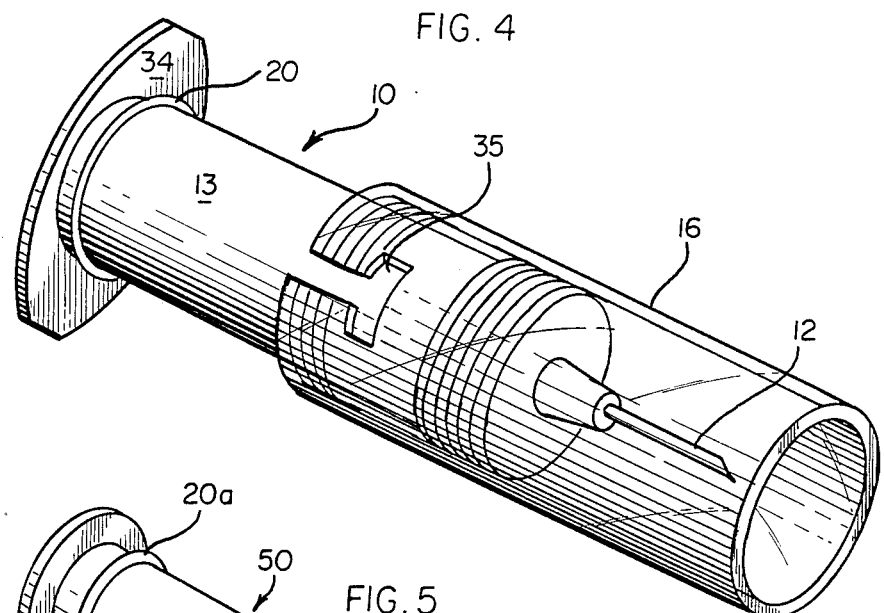
FIG. 4 is an isometric view of the phlebotomy tube of FIGS. 1-3 with the protective shield in the FIG. 1 position.

FIG. 4 illustrates a key-shaped cut-out 35 formed in the surface of shield 16, distal to needle 12. Cut-out 35 allows outward expansion of the second end portion 18 of shield 16 and thus facilitates mounting shield 16 onto the body of the phlebotomy tube, in that shield end portion 18 can be spread open to fit over teeth 29. Moreover, cut-out 35 provides some resiliency to shield 16. This resiliency permits downwardly-depending teeth 22 to "ratchet" past upwardly-extending teeth 29 when the shield is moved into the needle-covering position of FIG. 3, as cut-out 35 expands to allow this movement. The resiliency also serves to maintain tension between the interface of teeth 22 and teeth 29 which assists in firmly maintaining shield 16 in the secured position.

In the event that one should wish to re-use phlebotomy tube 10 (e.g., after a sterilization procedure), cut-out 35 facilitates removal of shield 16 by means of a tool.

Figure 5:
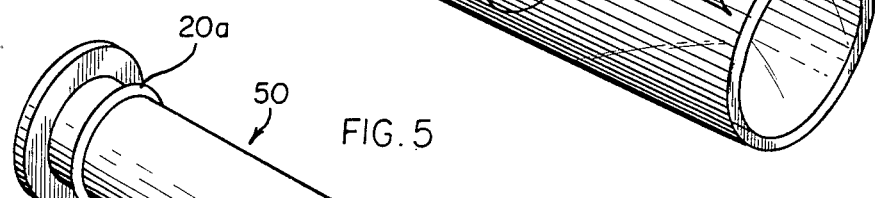
FIG. 5 is an isometric view of a shielded intravenous catheter placement unit having the shield in a releasable, needle-covering position.
Figure 6:
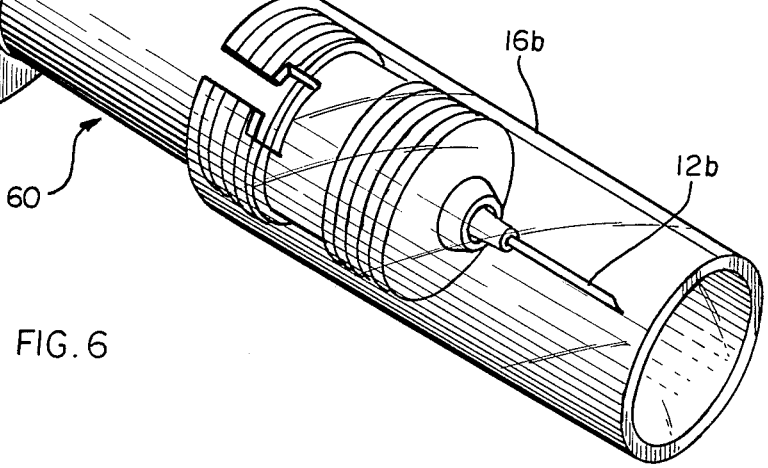
FIG. 6 is an isometric view of a shielded hypodermic syringe having the shield in a releasable, needle-covering position.

FIGS. 5 and 6 show two other embodiments of the medical device of the present invention—intravenous catheter placement unit 50 and hypodermic syringe 60. Catheter placement unit 50 and syringe 60 have tubular protective shields 16a, 16b slidably mounted around respective hollow needles 12a, 12b. As is the case with shield 16, used with phlebotomy tube 10, shields 16a and 16b are adapted to be moved from the first, releasable position illustrated in FIGS. 5 and 6 to an intermediate, releasable needle-exposing position (wherein shields 16a, 16b are held respectively by distal retaining rings 20a, 20b) and, after use, to a third, locked position.

FIGS. 7–10 show an alternative construction of a disposable phlebotomy tube 100 adapted with a protective shield 160. Phlebotomy tube 100 is constructed generally in the same manner as the apparatus depicted in FIGS. 1–4. The major difference between the apparatus of FIGS. 1–4 and the apparatus of FIGS. 7–10 is that the cylindrical wall 130 of the later apparatus is provided with a single, outwardly-extending, raked tooth 290 rather than a plurality of teeth 29 (compare FIGS. 1 and 7). Tooth 290 is located circumferentially around distal end section 300 of phlebotomy tube cylindrical wall 130. Outwardly extending raked tooth 290 is adapted to cooperate with the downwardly depending teeth 220 on the surface of a tubular protective shield 160 to lock the shield firmly in place around the needle after the apparatus has been used (See, FIG. 9).

Figure 7:
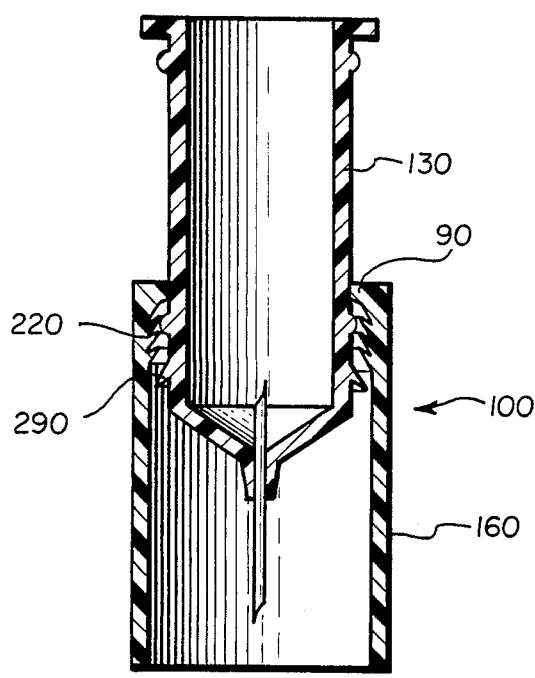
FIG. 7 is an elevational view, partly in section, of a second embodiment of a phlebotomy tube in accordance with the present invention wherein the tubular protective shield is in a first, releasable, needle-covering position.
Figure 8:
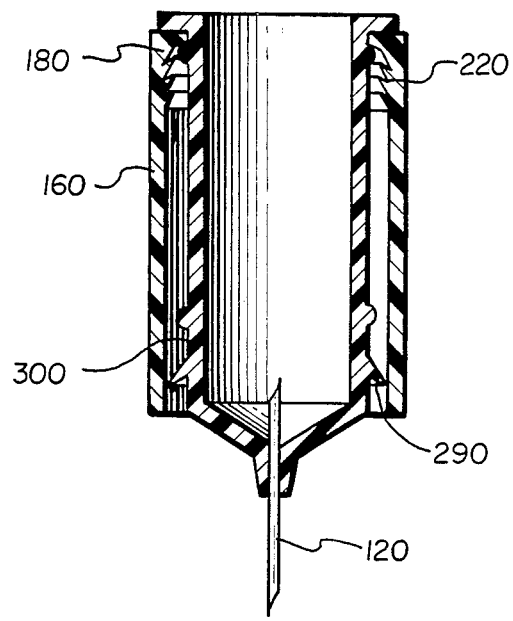
FIG. 8 is an elevational view of the apparatus of FIG. 7 with the protective shield in a second, releasable, needle-exposing position.

Another difference between the apparatus of FIG. 1 and that of FIG. 7 is that shield 160 is provided with an inwardly-depending shoulder portion 90 which extends radially around a second end portion 180 of shield 160. Shoulder portion 90 serves as a check or stop and prevents shield 160 from being inadvertently detached from tube 100 when the shield is advanced to the final, needle-covering position of FIG. 9.

Figure 10:
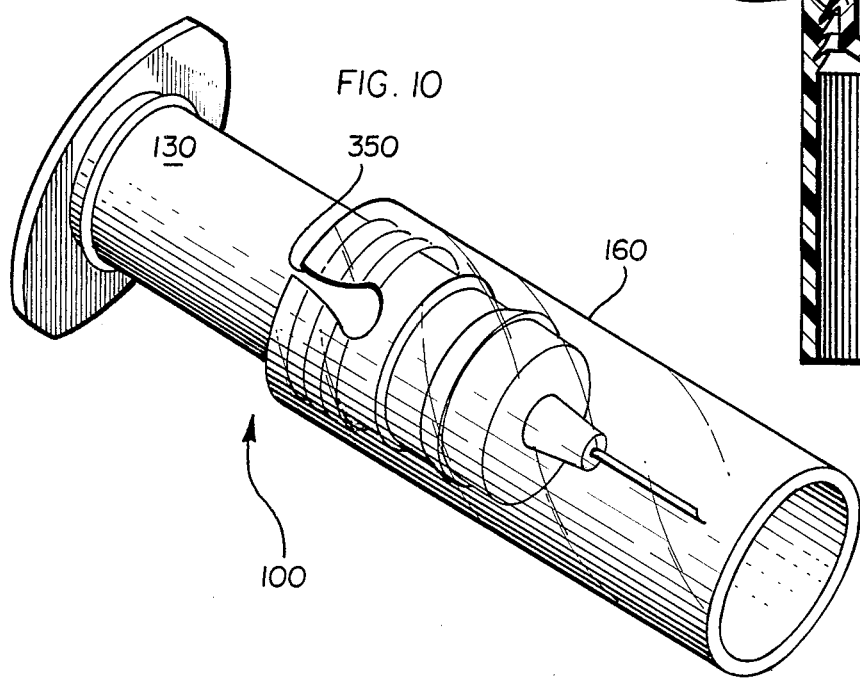
FIG. 10 is an isometric view of the phlebotomy tube of FIGS. 7-9 with the protective shield in the FIG. 7 position.

The final difference between the two embodiments is that shield 160 has a tear drop-shaped cut-out 350, formed in the surface of the shield of 160, distal to needle 120 (FIG. 10). Cut-out 350 facilitates the mounting of shield 160 onto the body of the phlebotomy tube in the same manner as key-shaped cut-out 35 in the apparatus of FIG. 4.

Figure 9:
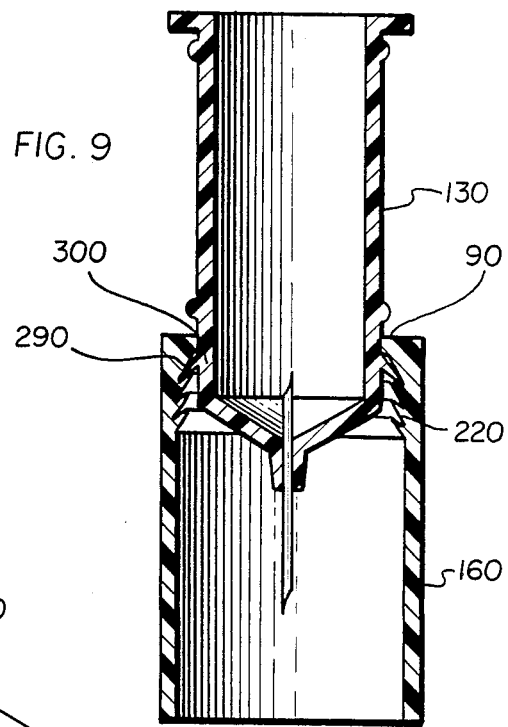
FIG. 9 is an elevational view, partly in section, showing the phlebotomy apparatus of FIG. 7 with the protective shield in a third, non-releasable, needle-covering position.

Like the apparatus shown in FIGS. 1–4, protective shield 160 can be moved to: (i) a releasable, needle-covering position (FIG. 7); (ii) a releasable, needle-exposing position (FIG. 8); and, (iii) a non-releasable, needle-covering position (FIG. 9). Operationally, therefore, the apparatus is identical to that of FIGS. 1–4.

Intravenous catheters, hypodermic syringes, and other elongated needle-bearing structures can be similarly modified to utilize a single, outwardly-extending, raised tooth on the tube portion of the apparatus, and a shoulder on the protective shield.

Various modifications, alternative constructions and equivalents may be employed without departing from the scope of the invention as exemplified in the foregoing description and further defined in the following claims.

What is claimed:

1. In a medical device comprising an elongated structure having proximal and distal end sections and an internal liquid passageway, a hollow needle having a point and an opposite end axially mounted at said proximal end section of the elongated structure in communication with said liquid passageway, and a tubular protective shield having first and second end portions, said shield mounted around a portion of said elongated structure and longitudinally movable from a needle-covering position, wherein the first end portion of said should extends beyond said needle point to a needle-exposing position, the improvement comprising:

a plurality of angular, inwardly-depending raked teeth circumferentially formed along an inner surface of the second end portion of said tubular protective shield;
   an angular, outwardly-extending raked tooth around the distal end section of said elongated structure, the angle of said outwardly-extending tooth being substantially complementary to the angle of the inwardly-depending teeth on said protective shield;
   a distal retaining ring extending annularly around the distal end section of said elongated structure for cooperating with said inwardly-depending teeth on said protective shield to releasably hold said shield in a needle-exposing position;
   an intermediate retaining ring extending annularly around said elongated structure, between said outwardly-extending teeth and said distal retaining ring, for cooperating with said inwardly-depending teeth on said protective shield to releasably hold said shield in a needle-covering position;
   an inwardly-depending shoulder portion extending radially around said second end portion of said tubular protective shield; and
   at least one cut-out in the surface of said protective shield for facilitating the mounting of said shield around said elongated structure.

2. A medical device according to claim 1 wherein said elongated structure comprises a hypodermic syringe.

3. A medical device according to claim 1 wherein said elongated structure comprises phlebotomy apparatus.

4. A medical device according to claim 1 wherein said elongated structure comprises an intravenous catheter placement unit.

5. A medical device according to claim 1 wherein said device is disposable.

6. A medical device according to claim 1 wherein said tubular protective shield is transparent.

7. Apparatus according to claim 6 wherein said shield comprises a thermoplastic material selected from the group consisting of acrylic plastics and polyethylene plastics.

8. A medical device according to claim 1 having a single cut-out, wherein said cut-out is adjacent said second end portion of said tubular shield.

9. A medical device according to claim 1 having at least two cut-outs in the surface of said protective shield, said cut-outs located adjacent said second end portion of said tubular shield.

10. A medical device according to claim 1 further including:
a protective cap removably mounted across an open end portion of said tubular shield.

11. Apparatus according to claim 1 wherein said inwardly-depending raked teeth are integral with said tubular shield.

* * * * *